United States Patent [19]

Balding et al.

[11] Patent Number: 4,731,260
[45] Date of Patent: Mar. 15, 1988

[54] HYDROPHOBIC FILTER MATERIAL AND METHOD

[75] Inventors: David P. Balding; Li-Chien Hsu, both of Mission Viejo; Sun De Tong, Tustin; Steven A. Craw, Mission Viejo, all of Calif.

[73] Assignee: American Hospital Supply Corporation, Evanston, Ill.

[21] Appl. No.: 683,252

[22] Filed: Dec. 18, 1984

[51] Int. Cl.[4] .............................................. B01D 13/04
[52] U.S. Cl. .............................. 427/236; 210/500.23; 210/500.36; 210/507; 210/508; 427/244
[58] Field of Search ............ 210/650, 651, 927, 500.2, 210/506, 507, 508, 500.21, 500.36, 500.23; 435/2; 427/236, 244, 246

[56] References Cited

U.S. PATENT DOCUMENTS

| 3,238,056 | 3/1966 | Pall et al. ............................ 210/506 |
| 3,568,846 | 3/1971 | Haefner ............................... 210/506 |
| 3,993,451 | 11/1976 | Verbeck ............................... 435/128 |
| 4,156,649 | 5/1979 | Quinn et al. ........................ 210/749 |
| 4,326,025 | 4/1982 | Buckles et al. ........................ 435/2 |
| 4,386,069 | 5/1983 | Estep .................................. 435/2 X |
| 4,411,783 | 10/1983 | Dickens et al. ................. 210/927 X |
| 4,458,042 | 7/1984 | Espy .................................... 162/146 |

OTHER PUBLICATIONS

ICI Americas Inc., General Characteristics of Surfactants, Brochure 0-1 10/80 5M 1963.

*Primary Examiner*—Richard V. Fisher
*Assistant Examiner*—W. Gary Jones
*Attorney, Agent, or Firm*—Gordon L. Peterson

[57] ABSTRACT

A filter material comprising hydrophobic filter media treated with a wetting agent which consists essentially of a material selected from the group consisting of polysobate 20, polysorbate 40, polysorbate 60 and polysorbate 80. The wetting agent is applied by dissolving it in a solvent and spraying the resulting solution onto the filter media.

2 Claims, 4 Drawing Figures

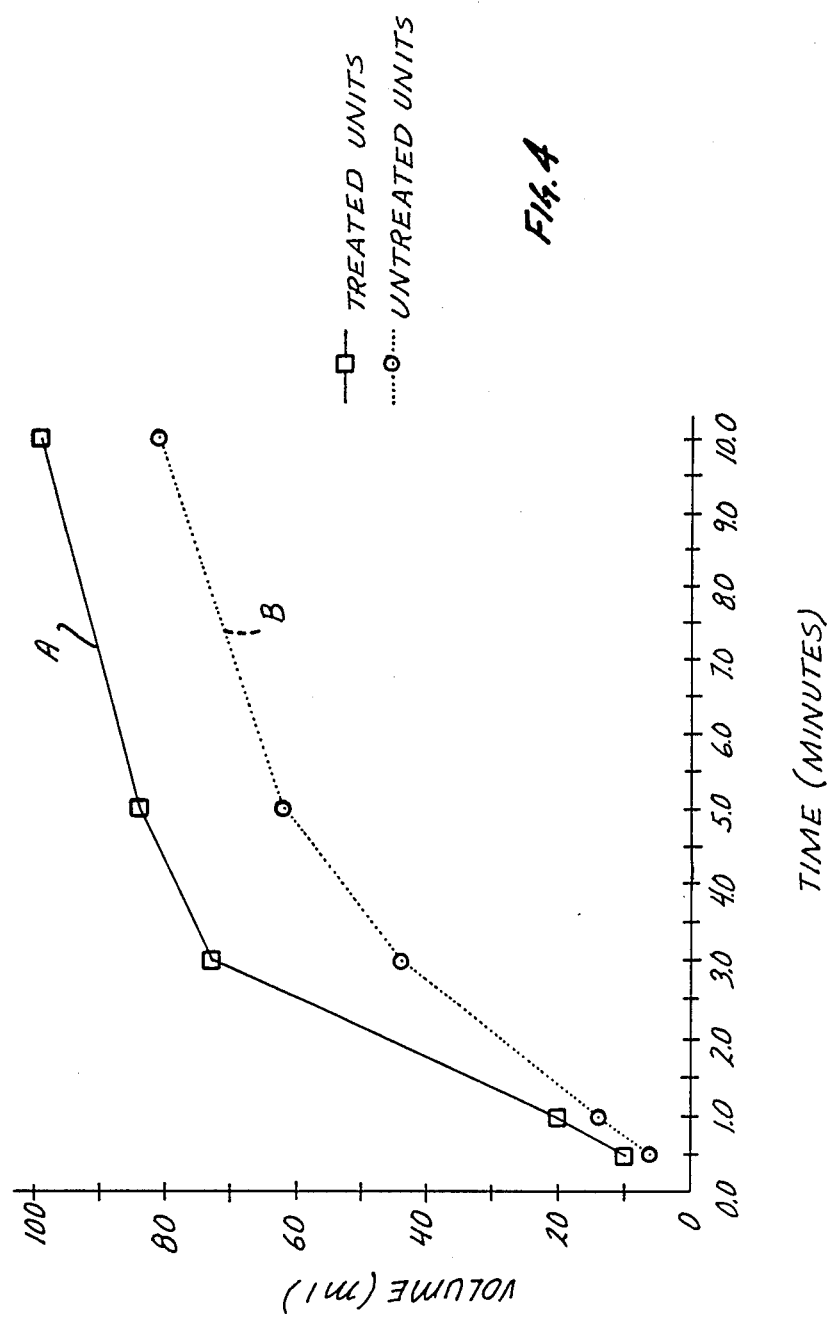

HYDROPHOBIC FILTER MATERIAL AND METHOD

BACKGROUND OF THE INVENTION

It is common practice to filter blood and other aqueous liquids by passing them through hydrophobic filter media. Hydrophobic materials, by their very nature, tend to reject aqueous liquids. Accordingly, one problem with use of hydrophobic filter media for the filtration of aqueous liquids is obtaining rapid filtration.

In one blood filtration process, blood to be filtered is introduced to the upstream side of the filter media, and it is desired to have the initial flow of the filtered blood, i.e., breakthrough from the downstream side of the filter media, as soon as possible. The hydrostatic head of blood above the filter media forms the driving force for the blood through the filter, and it is desired to obtain breakthrough with a minimum blood volume above the filter media, i.e., with a minimum hydrostatic head. Unfortunately, hydrophobic filter media resists the initial flow of blood through the media such that, in breakthrough tests, the time delay between the introduction of blood to the upstream side of the media and the initiation of flow through the media is longer than desired.

For industrial applications, a wetting agent can be deposited in the hydrophobic filter media to assist the flow of aqueous liquids through the media. However, the filtration of blood poses many unique problems which prevent the application of industrial wetting agents to the filter media. For example, the wetting agent must produce only minimal hemolysis and have no more than minimal complement activation. It must not induce abnormalities in blood coagulation or in platelet function, and because the filter media must be sterile, it must be compatible with gamma sterilization and ethylene oxide sterilization. The wetting agent must be, under the conditions of use, essentially nontoxic, noncytotoxic and nonpyrogenic, and it must not be a suspected carcinogen. The filter media, after being treated with the wetting agent, must pass United States Pharmacopeia (USP) Class VI and must not be unduly stiffened as a result of applying the wetting agent.

SUMMARY OF THE INVENTION

This invention solves these problems by using a wetting agent that consists essentially of polysorbate 20, polysorbate 40, polysorbate 60, polysorbate 80 or mixtures thereof. Such wetting agents and the filter media treated with such wetting agents meet all of the above-noted requirements for blood filtration.

Hydrophobic filter media treated with this wetting agent provides a filter material which can filter aqueous liquids much more rapidly than untreated filter media. In addition, breakthrough of blood through a hydrophobic filter media treated with the wetting agent of this invention occurs with about one-half the blood volume above the filter media that would be necessary with untreated hydrophobic filter media. Accordingly, for a given rate of blood supply to the filter media, breakthrough occurs much more rapidly with the treated filter media.

To apply the wetting agent, the wetting agent is first dissolved in a solvent to form a solution which is sprayed on the filter media. The solvent is then evaporated leaving the wetting agent on the filter media. Although aqueous solvents, such as purified water, can be used, to improve penetration of the hydrophobic filter media by the solution, to decrease drying time and to minimize pyrogen problems associated with aqueous solutions, the solvent is preferably a nonaqueous solvent and may be, for example, isopropanol, ethanol, methanol or 1,1,2 trichlorotrifluoroethane which is available under the trademark Freon.

The filter media could be dipped or immersed in the wetting agent-solvent solution. However, spraying is greatly preferred because spraying allows accurate control of the amount of wetting agent applied to the filter media. Immersing is also somewhat messy, tends to waste solvent and increases the time required for evaporation of the solvent.

To assure good penetration of the wetting agent-solvent solution into the filter media, it is preferred to spray both sides of the filter media. In one embodiment of the invention, first and second layers of filter media are joined together along three sides to form a tube having one end closed. Both the inside and outside of the two layers of filter media are sprayed with the solution, and in addition, some of the solution is deposited onto the interior of the tube adjacent the closed end. This assures a greater concentration of the wetting agent adjacent the closed end where flow requirements are expected to be greater. If desired, the concentration of the wetting agent in the solution which is deposited can be greater than the concentration of the wetting agent in the solution which is sprayed.

The wetting agents of this invention can be used with any hydrophobic filter media. The filter media is porous and may be of virtually any kind. For example, the filter media may be in the form of a woven screen, a nonwoven felt, a permeable or semipermeable membrane, open-cell foam or hollow fibers. The filter media may be a hydrophobic polymer, such as polypropylene, polyester, polyethylene, polyurethane and polytetrafluoroethylene. The treated filter media can be used in various different kinds of filters. Although the treated filter media is particularly adapted for use in a blood filter, it can be used to filter other aqueous liquids.

The invention, together with additional features and advantages thereof, can best be understood by reference to the following description taken in connection with the accompanying illustrative drawing.

BRIEF DESCRIPTION OF THE DRAWING

FIG. 4 is a plot of average flow volume versus time for treated and untreated filter media.

DESCRIPTION OF THE PREFERRED EMBODIMENT

Figure 1:
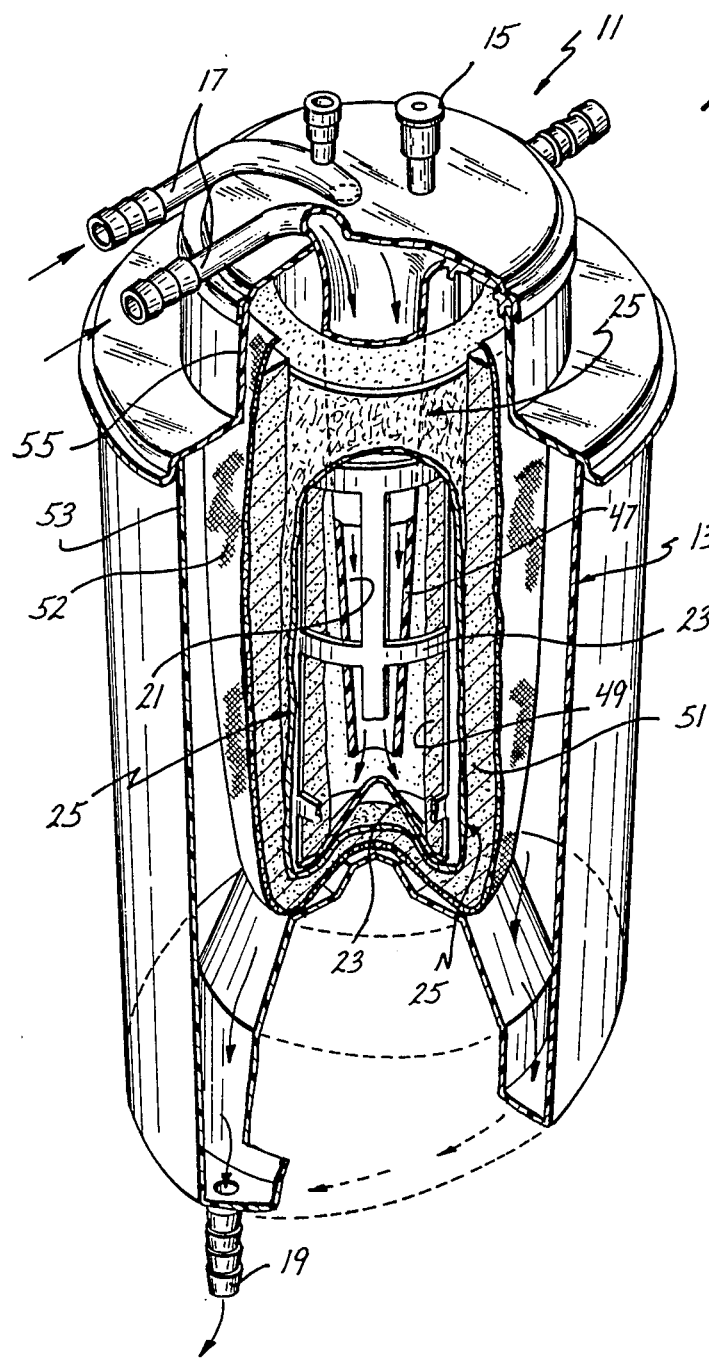
FIG. 1 is an isometric view with parts broken away showing a cardiotomy reservoir.

FIG. 1 shows a cardiotomy reservoir 11, which is one form of filter which can advantageously utilize the filter material of this invention. The reservoir 11 includes a housing 13 having multiple inlets 15 and 17, an outlet 19 and a flow path 21 extending between the inlets 15 and 17 and the outlet 19. An open support grid 23 is mounted within the housing, and filter material in the form of a filter tube 25 covers the grid 23.

Figure 2:
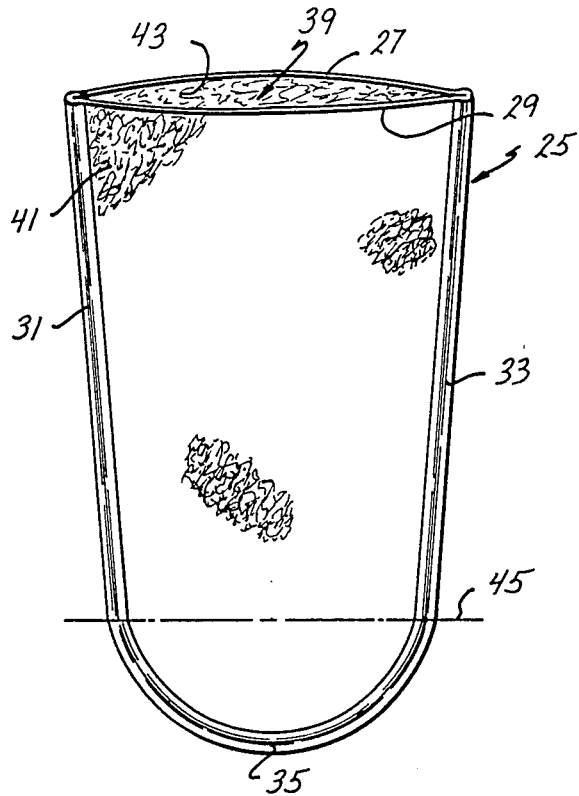
FIG. 2 is an isometric view of the treated filter media used in the cardiotomy reservoir.
Figure 3:
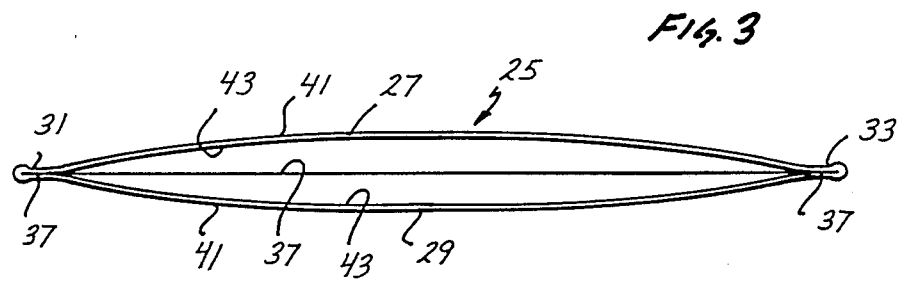
FIG. 3 is a top view of the filter media.

As shown in FIGS. 2 and 3, the filter tube 25 comprises layers 27 and 29 of hydrophobic filter media sealed together along opposite sides 31 and 33 and along one end 35 by a heat seal 37. Thus, the end 35 of the filter tube 25 is closed, and the filter tube has an end 39 which is open. In this embodiment, the layers 27 and 29 are constructed of felted polypropylene of the type which can be obtained from Lydall of Hamptonville, N.C. The felted polypropylene comprises short polypropylene fibers needled together randomly and then squeezed together between calendar rolls. One of the rolls is relatively hot to partially melt the fibers so that each of the layers 27 and 29 has an outer face 41 which has a harder surface than inner faces 43 of such layers.

The filter tube 25 has been treated with, and has impregnated therein, polysorbate 80 wetting agent. Greater amounts of the polysorbate 80 have been applied to the layers 27 and 29 adjacent the closed end 35. Specifically, regions below a reference line 45 generally have a greater concentration of the wetting agent. The location of the reference line 45 can be selected depending upon the region of the filter tube 25 which is to receive the greatest volume of aqueous liquid. Of course, the filter tube 25 is only one example of the kind of filter media to which the wetting agent can be applied.

To apply the polysorbate 80, it is dissolved in a solvent, which is preferably nonaqueous, to form a solution which is sprayed onto the outer faces 41 and inner faces 43. In addition, some of the solution is deposited onto the inner faces 43 below the reference line 45. The solution penetrates the filter media. The tube 25 is then air dried to evaporate the solvent and leave the wetting agent. The concentration of the polysorbate 80 in the solution which is deposited is greater than the concentration of the polysorbate 80 in the solution which is sprayed. The spraying and depositing steps are carried out with the tube 25 pulled over and mounted on the grid 23.

The cardiotomy reservoir 11 also includes an inlet conduit 47 coupled to all of the inlets 15 and 17 and projecting axially into the filter tube 25. The cardiotomy reservoir 11 may also include an inner defoamer 49 within the filter tube 25, an outer defoamer 51 outside of the filter tube, and an outer porous sock 52. The housing 13 may comprise one or more sections, and in the embodiment shown, it includes a body section 53 and a cover section 55. Except for the treated filter tube 25, the cardiotomy reservoir 11 may be of conventional construction.

The cardiotomy reservoir 11 is then sterilized using conventional techniques, such as gamma sterilization and ethylene oxide sterilization. In either event, the filter tube 25 would survive the sterilization with a minimal detrimental effect.

The cardiotomy reservoir 11 is used in a conventional manner by introducing blood from a donor and/or saline through the inlet 15 and blood from the surgical field through the inlets 17. The blood passes into the filter tube 25 and accumulates above the closed end 35 until a sufficient hydrostatic head is obtained to cause the blood to pass through the filter tube. The filtered blood then flows by gravity through the outlet 19 through the filter tube 25 and out the outlet 19. Because of the presence of the polysorbate 80 on the filter tube 25, the blood can pass through the filter tube much more rapidly than if the filter tube 25 were not treated with the polysorbate 80. Also, the breakthrough volume is much lower than if the filter tube 25 were not treated with the polysorbate 80. In other words, the flow of blood at the outlet 19 will first appear with a lower volume of blood in the bottom of the filter tube 25 and hence a lower hydrostatic head.

The polysorbate 80 wetting agent is an oleate ester of sorbitol and its anhydrides copolymerized with approximately twenty moles of ethylene oxide for each mole of sorbitol and sorbitol anhydrides. Its structural formula is as follows:

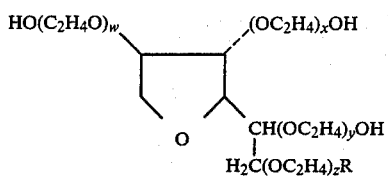

[Sum of w, x, y, z is 20; R is $(C_{17}H_{33})COO$]

Polysorbate 20, polysorbate 40, and polysorbate 60 are very similar chemically to polysorbate 80 and are also blood compatible in that they all meet the blood filtration requirements set forth herein. Similarly, mixtures of any two or more of polysorbate 20, polysorbate 40, polysorbate 60 and polysorbate 80 would also meet the blood filtration requirements set forth herein.

Polysorbate 20, which may also be used as the wetting agent, is a laurate ester of sorbitol and its anhydrides copolymerized with approximately twenty moles of ethylene oxide for each mole of sorbitol and sorbitol anhydrides. Its structural formula is as follows:

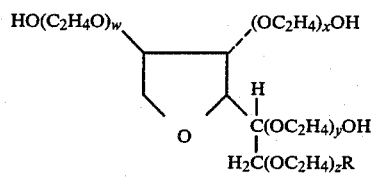

[Sum of w, x, y, and z is 20; R is $(C_{11}H_{23})COO$]

Polysorbate 40 is a palmitate ester of sorbitol and its anhydrides copolymerized with approximately twenty moles of ethylene oxide for each mole of sorbitol and sorbitol anhydrides. Polysorbate 60 is a mixture of stearate and palmitate esters of sorbitol and its anhydrides copolymerized with approximately twenty moles of ethylene oxide for each mole of sorbitol and sorbitol anhydrides.

EXAMPLE I

A dipping solution was prepared by dissolving 5 g of polysorbate 80 in 5 liters of purified water. A felted polypropylene filter medium similar to the filter tube 25 was soaked in the dipping solution for five minutes. After the soaking time, the filter tube was taken out and the excessive water on the filter tube was squeezed out through a roller wringer action. The filter tube was then dried in an air-circulated oven.

The polypropylene filter tube was then placed over a grid, such as the grid 23. The treated filter tube was tested to determine its relative wettability by pumping saline into the top of the filter tube subassembly and observing the volume in the filter tube required to wet through the filter tube ("breakthrough volume"). This testing procedure was carried out eleven times for treated filter tubes and six times for untreated felted polypropylene filter tubes.

Generally, about a twofold improvement in breakthrough volume was observed for the treated filter tube as compared with the untreated filter tube. The average breakthrough volume for the eleven treated filter tubes was 123 ml, and the average breakthrough volume for the six untreated filter tubes was 262 ml. In addition, the rate of flow through the treated filter tube was higher than through the untreated filter tube.

EXAMPLE II 2 ml of a 0.5 percent (weight/volume) solution of polysorbate 80 in a 96 percent (volume/volume) 1,1,2 trichlorotrifluoroethane and 4 percent (volume/volume) ethyl alcohol solvent was sprayed onto the inner faces and 2 ml of the same solution was sprayed onto the outer faces of a felted polypropylene filter tube similar to the filter tube 25 after the latter had been placed over a grid, such as the grid 23. Then 2 ml of a 1.0 percent (weight/volume) solution of polysorbate 80 in the same kind of solvent was deposited on the inner faces of the filter tube below the reference line 45 to achieve a total of 40 mg polysorbate 80 on the filter tube-grid assembly. The filter tube was then air dried until the solvent evaporated.

Nine of the thus treated filter tubes were tested as described in Example I. The average breakthrough volume for the treated filter tubes was 67 ml.

EXAMPLE III

Example II was repeated, except that the filter tubes were made of felted polyester. The average breakthrough volume for 36 entire cardiotomy reservoirs, such as the reservoir 11, containing treated felted polyester filter tubes was 107 ml, and the average breakthrough volume for 3 identical cardiotomy reservoirs containing untreated polyester filter tubes was 149 ml. Because of the less hydrophobic nature of polyester compared to polypropylene, breakthrough volumes would be expected to be lower for untreated polyester than untreated polypropylene.

EXAMPLE IV

A 0.5 percent (weight/volume) solution of polysorbate 20 in the same kind of solvent as in Example II and a 1 percent (weight/volume) solution of polysorbate 20 in the same kind of solvent could be applied to a polypropylene filter tube as in Example II and would be expected to give similar test results relating to breakthrough volume.

EXAMPLE V

A solution of 1 percent (weight/volume) polysorbate 80 can be prepared by dissolving 50 g of polysorbate 80 in 5 liters of alcohol. 3.5 liters of this solution can be mixed with 1.5 liter of 1 percent (weight/volume) polysorbate 20 solution as described in Example IV. The mixture is 1 percent (weight/volume) in polysorbate, which is constituted of 70 percent polysorbate 80 and 30 percent polysorbate 20.

This polysorbate 80-20 mixture could be applied to a polypropylene filter tube as in Example II and would be expected to give similar test results relating to breakthrough volume.

FIG. 4 is a graph showing average blood volume through the cardiotomy reservoir 11 following saline prime as a function of time. The curve A is for a cardiotomy reservoir using a filter tube 25 treated generally in accordance with Example II, and the curve B is for the cardiotomy reservoir 11 utilizing an untreated filter tube 25. Each of the curves was plotted by introducing a 100 ml blood sample into the inlet 17 and periodically measuring the volume of blood thereafter passing through the outlet 19 into a receptacle. This procedure was carried out on several cardiotomy reservoirs having treated and untreated filter tubes 25, and both the curves A and B represent the average of these several tests. From FIG. 4, it can be seen that much more rapid filtration is achieved with the filter tube treated in accordance with the teachings of this invention.

Although an exemplary embodiment of the invention has been shown and described, many changes, modifications and substitutions may be made by one having ordinary skill in the art without necessarily departing from the spirit and scope of this invention.

I claim:

1. A method of making blood filter material comprising spraying a solution which includes a wetting agent and a solvent on hydrophobic filter media and evaporating the solvent leaving the wetting agent on the filter media, said wetting agent consisting essentially of material selected from the group consisting of polysorbate 20, polysorbate 40, polysorbate 60, polysorbate 80, and mixtures thereof, said filter media including first and second layers of filter media joined together along three sides to form a tube having one end closed, said step of spraying including spraying the inside and outside of the first and second layers of filters media at least adjacent the closed end, and said method including, additionally to said spraying step, depositing an additional solution of said wetting agent and said solvent onto the interior of the tube adjacent the closed end.

2. A method as defined in claim 1 wherein the concentration of the wetting agent in the solution which is sprayed is less than the concentration of the wetting agent in the additional solution which is deposited.

* * * * *